US010265277B2

(12) United States Patent
Carberry

(10) Patent No.: US 10,265,277 B2
(45) Date of Patent: *Apr. 23, 2019

(54) COMPOSITION OF OLIVETOL AND METHOD OF USE TO REDUCE OR INHIBIT THE EFFECTS OF TETRAHYDROCANNABINOL IN THE HUMAN BODY

(71) Applicant: Undoo, LLC, Mesa, AZ (US)

(72) Inventor: James J. Carberry, Mesa, AZ (US)

(73) Assignee: UNDOO, LLC, Mesa, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/956,659

(22) Filed: Apr. 18, 2018

(65) Prior Publication Data

US 2018/0235905 A1   Aug. 23, 2018

Related U.S. Application Data

(63) Continuation-in-part of application No. 15/417,179, filed on Jan. 26, 2017, which is a continuation of application No. 15/360,389, filed on Nov. 23, 2016, now Pat. No. 9,918,947.

(60) Provisional application No. 62/258,979, filed on Nov. 23, 2015.

(51) Int. Cl.
*A61K 31/05* (2006.01)
*A61K 9/48* (2006.01)
*A61K 9/00* (2006.01)
*A61K 9/127* (2006.01)

(52) U.S. Cl.
CPC ............ *A61K 31/05* (2013.01); *A61K 9/0053* (2013.01); *A61K 9/127* (2013.01); *A61K 9/4825* (2013.01); *A61K 9/4858* (2013.01); *A61K 9/4875* (2013.01)

(58) Field of Classification Search
None
See application file for complete search history.

(56) References Cited

U.S. PATENT DOCUMENTS 3,734,930 A * 5/1973 Razdan ............... C07D 311/80
549/390

OTHER PUBLICATIONS

C. E. Turner, M. H. Elsohly, E.G. Boeren. Constituents of Cannabis Sativa L. XVII. A Review of the Natural Constituents. J. Nat. PRod 43.2 (1980) 169-234. (Year: 1980).*
E. A. Formukong, A. T. Evans, and F. J. Evans. Inhibition of the cataleptic effect of tetrahydrocannabinol by other constituents of Cannabis sativa L. J. Pharm. Pharmacol. 1988.40: 132-134. (Year: 1988).*

* cited by examiner

*Primary Examiner* — Michael P Cohen
(74) *Attorney, Agent, or Firm* — Lapple Ubell IP Law, LLP; Matthew C. Lapple

(57) ABSTRACT

Embodiments of the present invention relate to the use of a therapeutically-effective amount of Olivetol to reduce, eliminate, inhibit or alleviate the psychoactive effects of THC in users of *Cannabis*. Further embodiments of the present invention relate to a softgel, tablet or capsule of Olivetol in combination with an edible oil.

20 Claims, No Drawings

COMPOSITION OF OLIVETOL AND METHOD OF USE TO REDUCE OR INHIBIT THE EFFECTS OF TETRAHYDROCANNABINOL IN THE HUMAN BODY

CROSS REFERENCE TO RELATED APPLICATIONS

The subject application is a continuation-in-part and claims priority to U.S. Provisional Patent Application Ser. No. 62/258,979, filed on Nov. 23, 2015, and U.S. Non-provisional patent application Ser. No. 15/360,389, filed on Nov. 23, 2016, now issued U.S. Pat. No. 9,918,947, and U.S. Non-provisional patent application Ser. No. 15/417,179, filed on Jan. 26, 2017, which applications are incorporated herein in their entirety by this reference thereto.

TECHNICAL FIELD

The embodiments herein relate generally to use of the compound Olivetol to reduce, alleviate, or inhibit the psychoactive effects of tetrahydrocannabinol in humans or other mammals.

BACKGROUND ART

Cannabis, also commonly known as marijuana, is a flowering plant that includes three species or sub-species, namely sativa, indica and ruderalis. The plant is indigenous to Central Asia and the Indian Subcontinent. Cannabis has long been used for hemp fiber, for oils, for medicinal purposes and as a recreational drug. Cannabis plants produce a group of chemicals called cannabinoids. The majority of these compounds are secreted by glandular trichromes that occur abundantly on the floral calyxes and bracts of female Cannabis plants. When used by humans medicinally or recreationally, Cannabis is typically consumed either by eating or smoking dried flower buds, resin, or various extracted oils or waxes.

The most well-known cannabinoid is tetrahydrocannabinol, often abbreviated as "THC." The chemical formula for THC is $C_{21}H_{30}O_2$ and it has the following chemical structure:

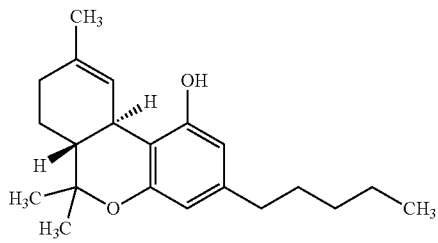 [SMILES: CCCCCc1cc(O)c2c(c1)OC(C)(C)[C@@H]1CCC(C)=C[C@@H]21]

THC is widely recognized as the principal psychoactive constituent in Cannabis. However, the Cannabis plant produces hundreds of other cannabinoids, terpenoids and other compounds that are only beginning to be identified, studied and categorized. It is believed by researchers that many of these other cannabinoids, terpenoids and other compounds may have important health benefits and/or be capable of treating certain human diseases.

There are two characterized cannabinoid receptors in the human body, CB1, which is primarily located in the central nervous system, and CB2 which is primarily located in the immune system and blood cells. These cannabinoid receptors are naturally present and are activated by endocannabinoids that are produced by the human body for neural and cell signaling. In neurons, endocannabinoids bind to the CB1 receptors at the pre-synaptic junction and, among other effects, impact the release of gamma-amino butyric acid ("GABA"). However, when THC is present in the human bloodstream, it binds to these cannabinoid receptors and causes many different psychotropic effects. Consumption of Cannabis by a human generally results in a wide variety of psychotropic effects, which is often referred to as a "high." The cannabis high varies depending on many factors, including the strain of Cannabis, the amount consumed, the method of consumption, the biochemistry of the individual consuming it and the individual's level of experience in consuming cannabis. That said, a cannabis high can include euphoria, anxiety, a general alteration of conscious perception, feelings of well-being, relaxation or stress reduction, increased appreciation of humor, music (especially discerning its various components/instruments) or the arts, joviality, metacognition and introspection, enhanced recollection (episodic memory), increased sensuality, increased awareness of sensation, increased libido, and creativity. Abstract or philosophical thinking, disruption of linear memory and paranoia or anxiety are also typical effects.

Cannabis consumption also often produces many subjective and highly tangible effects, such as greater enjoyment of food taste and aroma, an enhanced enjoyment of music and comedy, and marked distortions in the perception of time and space (where experiencing a "rush" of ideas from the bank of long-term memory can create the subjective impression of long elapsed time, while a clock reveals that only a short time has passed). Many individuals find some of these effects pleasing and enjoyable, while other individuals do not enjoy such effects.

Although Cannabis has a high margin of safety, it can produce negative side effects. At higher doses in humans, effects can include altered body image, auditory and/or visual illusions, pseudo-hallucinatory, and ataxia from selective impairment of polysynaptic reflexes. In some cases, in humans, cannabis can lead to dissociative states such as depersonalization and derealization. Additionally, canine studies of very high doses of cannabis resulted in intoxication effects including depression, hypersalivation, mydriasis, hypermetria, vomiting, urinary incontinence, tremors, hypothermia, bradycardia, nystagmus, agitation, tachypnea, ataxia hyperexcitability and seizures. Occasionally, heavy use, or use by inexperienced human consumers, particularly in an unfamiliar environment, can result in very negative experiences. Any episode of acute psychosis that accompanies cannabis use usually abates after 6 hours, but in rare instances heavy users may find the symptoms continuing for many days. If the episode is accompanied by aggression or sedation, physical restraint may be necessary.

No known antidote presently exists for THC overconsumption or intoxication, nor any known medications for treating cannabis dependence or withdrawal. Efforts have been made to discover or develop such an antidote or medication, including experiments with Nabiximols, Pregnenolone, Rimonabant, and with intralipid therapy to bind to the highly lipophilic THC, none of which have proven satisfactory. Other effects of THC and efforts to identify antagonists to endocannabinoid receptors are discussed in the paper, "Phytocannabinoids and Endocannabinoids," Fišar, Zdeněk, CURRENT DRUG ABUSE REVIEWS (2009) 2, 51-75, which is hereby incorporated by reference as if set forth fully herein. Similarly, the paper "Phytocannabinoids Beyond the *Cannabis* Plant—do they exist?" Gertsch, Jürg et al., BRITISH JOURNAL OF PHARMACOLOGY (2010) 160, 523-529, describes other compounds which may interact directly or indirectly with cannabinoid receptors, and which is hereby incorporated by reference as if fully set forth herein.

While many psychoactive drugs clearly fall into the category of either stimulant, depressant, or hallucinogen, *cannabis* exhibits a mix of all properties, perhaps leaning the most towards hallucinogenic or psychedelic properties, though with other effects quite pronounced as well. THC is typically considered the primary active component of the *cannabis* plant; various scientific studies have suggested that certain other cannabinoids like CBD may also play a significant role in its psychoactive effects.

In the early twentieth century, it became illegal in most of the world to cultivate or possess *Cannabis*. However, within the last decade, some states and nations have begun to legalize the cultivation, possession and use of *Cannabis* for medical purposes. *Cannabis* is used to reduce nausea and vomiting during chemotherapy, to improve appetite in people with HIV/AIDS, to treat chronic pain, and help with muscle spasms. Other possible medical uses, which are sometimes disputed, include treatment of multiple sclerosis, AIDS wasting syndrome, epilepsy, rheumatoid arthritis, glaucoma, PTSD, depression and generalized anxiety. However, many patients are hesitant to try or continue to consume *cannabis* due to a desire to avoid the perceived negative psychotropic effects of a *cannabis* high. Accordingly, there is a need to address the negative, unpleasant or undesired psychotropic effects of *cannabis* consumption, while allowing individuals to still be able to consume it for medical reasons and its health benefits.

Further, within the last two years, several states in the United States have legalized or decriminalized the cultivation, possession and use of *Cannabis* for recreational purposes. As such, some sources estimate that there are many more recreational users of *Cannabis* than ever before, including new or otherwise inexperienced consumers of *Cannabis*. Further, with the increased availability of *Cannabis*, some experienced users may choose to increase their consumption levels. Because some of the perceived negative psychotropic effects of *cannabis* consumption can be more pronounced or frightening to inexperienced *cannabis* users, or heavy *cannabis* users, there is a need for a way or compound that can reduce, alleviate or inhibit the psychotropic effects of *cannabis* after it has been consumed, or after it has been consumed in a larger than recommended or desired amount.

Olivetol (also known as 5-pentylresorcinol or 5-pentyl-1,3-benzenediol, 5-n-Amylresorcinol, and 3,5-Dihydroxyamylbenzene) is a naturally occurring organic compound. The Olivetol chemical formula is $C_{11}H_{16}O_2$ and it has the following chemical structure:

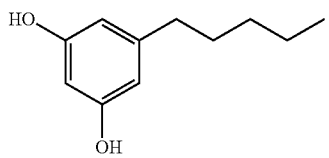

Olivetol is found in certain species of lichens and can be readily extracted. Olivetol is also produced by a number of insects, either as a pheromone, repellent, or antiseptic. The *Cannabis* plant internally produces the related substance olivetolic acid (OLA). Both Olivetol and OLA can be synthesized in the laboratory. It has been hypothesized that the *Cannabis* plant in turn utilizes OLA as a component in its biosynthesis of THC. Further information and explanation of Olivetol and OLA are provided in the published paper, "In Vitro And In Vivo Pharmacology Of Synthetic Olivetol-Or Resorcinol-Derived Cannabinoid Receptor Ligands, M. G. Gascio et al., BRITISH JOURNAL OF PHARMACOLOGY (October 2006) 149(4); 431-440, which is hereby incorporated by reference as though fully set forth herein. Olivetol has been successfully used as a precursor in various laboratory syntheses of THC. However, literature searches reveal no known uses of Olivetol for medicinal or other human consumption purposes.

As such, there is a need for a way or compound that can reduce, alleviate or inhibit the psychotropic effects of *cannabis* after it has been consumed, or after it has been consumed in a larger than recommended amount.

SUMMARY OF INVENTION

Embodiments of the present invention relate to the use of a therapeutically-effective amount of Olivetol, and/or OLA, in some cases combined with other compounds, in various forms for delivery, to reduce, eliminate, inhibit or alleviate the psychoactive effects of THC in users of *Cannabis*.

DESCRIPTION OF EMBODIMENTS

Olivetol, also known as 5-pentylresorcinol or 5-pentyl-1,3-benzenediol, is a naturally occurring compound with structures analogous to THC. The inventors have demonstrated that consumption of Olivetol, either before or after consumption of THC, will significantly reduce the psychotropic effects of THC ingestion.

It is believed that Olivetol acts as a competitive inhibitor of the cannabinoid receptors CB1 and CB2. Due to its smaller size and its lack of more functional groups, it is believed that Olivetol binds more tightly and/or more aggressively to the cannabinoid receptors CB1 and/or CB2 and has a much lower dissociation constant, allowing it to stay in the active site of the CB receptors for a longer period of time while not activating the receptor, thereby not causing the change in GABA release that is believed to be the mechanism of THC's psychotropic effects.

Olivetol can be consumed following THC ingestion to significantly reduce the psychotropic and other effects of THC, and it is believed that it can be consumed prior to THC ingestion, to dampen these psychotropic and other effects. The range for an effective dose of Olivetol is 8 mg to 100 mg, with the preferred range between 30 mg and 60 mg. However, for certain individuals, larger or smaller doses may be effective, or necessary, suggesting an effective dose range of Olivetol between 4 mg to 200 mg. Further, in cases of extreme consumption of THC, even higher does may be advantageous. A dose approaching 10-15 mg/kg may be advantageous.

Olivetol is a fat soluble compound that should be combined with and consumed with a human-consumable fatty oil for best absorption in the gastrointestinal tract including in the stomach and small intestine. Any edible oil in which the Olivetol molecule will dissolve will suffice. In one embodiment, Olivetol is mixed with and/or dissolved in olive oil. However other edible oils are suitable, including major food oils such as vegetable, canola, peanut, almond, coconut, avocado, sesame, corn, cottonseed, palm, safflower, rapeseed, soybean, and sunflower; nut oils such as almond, beech nut, brazil nut, cashew, hazelnut, *macadamia*, mongongo nut, pecan, pine nut, pistachio, and walnut; citrus oils such as grapefruit seed oil, lemon oil, and orange oil; oils from melon and gourd seeds including from the members of the Cucurbitaceae family, such as bitter gourd oil, bottle gourd oil, buffalo gourd oil, butternut squash seed oil, egusi seed oil (from *Cucumeropsis mannii naudin* seeds), pumpkin seed oil and watermelon seed oil; food supplement oils such as Açaí oil (from fruit of several species of the Açaí palm), black seed oil (pressed from *Nigella sativa* seeds), blackcurrant seed oil (from *Ribes nigrum* seeds), borage seed oil (from *Borago officinalis* seeds), evening primrose oil (from *Oenothera biennis* seeds), and flaxseed oil (or linseed oil)(from *Linum usitatissimum* seed); or other known edible oils such as amaranth seed oil (from sees of grain amaranth species including *Amaranthus cruentus* and *Amaranthus hypochondriacus*), apricot oil, apple seed oil, argan oil (from the seeds of the *Argania spinosa*), artichoke, avocado, babassu oil (from the seeds of the *Attalea speciosa*), ben oil (from the seeds of *Moringa oleifera*), Borneo tallow nut oil (extracted from the fruit of species of genus *Shorea*), cape chestnut oil (also called yangu oil), carob pod oil (*Algaroba* oil), cocoa butter, cocklebur oil (from species of genus *Xanthium*), cohune oil (from *Attalea cohune*), coriander seed, date seed oil, dika oil (from *Irvingia gabonensis* seeds), false flax oil (from *Camelina sativa* seeds), grape seed oil, hemp oil, kapok seed oil (from *Cieba pentandra* seeds), kenaf seed oil (from *Hibiscus cannabinus* seeds), *lallemantia* oil (from *Lallemantia iberica* seeds), mafura oil (from *Trichilia emetica* seeds), marula oil (from *Sclerocarya birrea* kernel), meadowfoam seed oil, mustard oil, niger seed oil (including from *Guizotia abyssinica*), nutmeg butter (extracted by expression form the fruit of cogeners of genus *Myristica*), nutmeg oil, okra seed oil (from *Abelmoschus esculentus* seeds), *papaya* seed oil, *papaya* oil produced by maceration, *perilla* seed oil, persimmon seed oil (including from *Diospyros virginiana*), pequi oil (from *Caryocar basiliense* seeds), pili nut oil (from *Canarium ovatum* seeds), pomegranate seed oil (from *Punica granatum* seeds), poppy seed oil, pracaxi oil (from *Pentaclethra macroloba* seeds), prune kernel oil, peach kernel oil, *quinoa* oil, ramtil oil (from one of several species of genus *Guizotia abyssinica* seeds), rice bran oil, royle oil (from *Prinsepia utilis* seeds), sacha inchi oil, sapote oil, seje oil (from *Jessenia bataua* seeds), shea butter, taramira oil (from arugula or *Eruca sativa* seeds), tea seed oil (camelia oil), thistle oil (from *Silybum marianum* seeds), Tigernut oil (or nut-sedge oil, from the *Cyperus esculentus* tuber), tobacco seed oil (from *Nicotiana* species seeds, if purified), tomato seed oil, and wheat germ oil. It will be understood that the above list is exemplary, and not meant to be limiting.

The effects of Olivetol on a person who has ingested THC will include but are not limited to clarity of mind, improved vision, increased ability to focus, improved motor skills, and reduction in any other symptoms of THC consumption.

A number of real-life, non-clinical trials have been performed by volunteers, to test the effects of the consumption of embodiments of the present invention, the conditions and results of which are described as follows. All tests were performed in "real life," rather than clinical conditions. Various methods of consumption of *cannabis* were used, such as consumption of edibles, inhalation of *cannabis* smoke, or inhalation of vapor, depending upon the volunteer's preference. Some subjects reported their pre-consumption mood, pain level, etc., as well as their level of experience with consumption of *cannabis*. After sufficient exposure to *cannabis*, each subject indicated when their euphoria or "high" had reached a high level or a peak. Then, the subject took one or more oral doses of an embodiment of the present invention, containing 30 mg of Olivetol combined with edible oil in a "softgel" pill. A timer was started and the subject then reported when they felt an awareness of a decrease or reduction in their euphoria or other *cannabis* effects, as well as their subjective feelings, mood, pain level or other observations, until they self-reported that their *cannabis* effects were concluded. In the majority of cases, subjects noticed a reduction in the effects of *cannabis* consumption between four to ten minutes, and most commonly six to seven minutes, after taking a dose of an embodiment of the present invention. Most subjects reported some improved level of mental clarity. However, most subjects also reported that the beneficial effects of their *cannabis* consumption, such as improved mood or pain reduction, remained even after the euphoric feeling and other physical effects associated with *cannabis* use declined following their use of a dose or two of an embodiment of the present invention.

In a first set of informal testing, volunteer testers provided the following information about their experiences, which were set forth in the attachments to the provisional patent application to which this application claims priority and which are summarized as follows:

Example 1A

Subject JS, inhaled *cannabis* smoke, from the strain "Kush." At the time of initial exposure to *cannabis*, subject had a mild headache, was slightly melancholy, and a bit tired. Thirty minutes after inhalation of *cannabis* smoke, subject reported mild euphoria and a loss of coordination and balance. At forty-five minutes after inhalation of *cannabis* smoke, subject reported subject's high had peaked, subject was euphoric, and subject's headache was resolved. At this peak of the high, the subject took one softgel of an embodiment of the present invention. Within ten minutes after the dose, subjected reported an awareness of a reduction in subject's high. Subject noted "head clears, body still unstable." Within thirty minutes after the dose, subject reported subject had returned to initial status, but that subject had "no headache, no melancholy, no change in energy." At one hour and fifteen minutes after the dose, subject reported that subject's high began to return and reported "loss of balance, coordination, mild euphoria." At that time, subject took a second capsule of an embodiment of the present invention. Within fifteen minutes after the second dose, subject reported that subject's high began to decline, and that "head clears, body still unstable." Within thirty minutes of the second dose, subject reported that subject had returned to initial status and "body returns to function."

Example 1B

Subject KD, inhaled *cannabis* smoke, from the strain "GS Cookies" as well as "Kief." Subject self-reported as an occasional consumer of *cannabis*. At the time of initial exposure to *cannabis*, subject reported that subject was "calm, balanced." Within two minutes after inhalation of *cannabis* smoke, subject reported onset of a *cannabis* high and noted that subject's heartbeat and pulse were increased. Seven minutes after inhalation of *cannabis* smoke, subject reported a peak *cannabis* high and took a first softgel of an embodiment of the present invention, for a dose of 30 mg of Olivetol. Within nine minutes after the dose, subjected reported an awareness of a reduction in subject's high.

Subject noted "heartbeat quiets." Within seventeen minutes after the dose, subject reported subject had returned to initial status and that subject was thirsty. Within thirty-eight minutes after the dose, subject reported that subject's high began to return. Within fifty-five minutes after the dose, however; subject reported that subject's high began to decline again. Within approximately seventy-six minutes after the dose, subject reported that subject had returned to initial status and was "ok to drive." At one-hundred and six minutes after the dose, the subject reported "ready to leave."

Example 1C

Subject JM, inhaled *cannabis* smoke, from the strain "GS Cookies" as well as "Kief." At the time of initial exposure to *cannabis*, subject was "relaxed," "not high" and reported having consumed a full meal approximately two hours earlier. Five minutes after inhalation of *cannabis* smoke, subject reported the beginning of a *cannabis* high and that subject felt "euphoria, relaxation, mind high, dry mouth, eyes." Fourteen minutes after inhalation of *cannabis* smoke, subject reported, subject reported subject's high had peaked, and noted that "laser light cat play distracting." At this peak of the high, the subject took one softgel of an embodiment of the present invention, for a dose of 30 mg of Olivetol. Within six minutes after the dose, subjected reported an awareness of a reduction in subject's high. Subject noted "lessening of frontal brain euphoria" and "eyes watering slightly." Within thirty-two minutes after the dose, subject reported that subject had returned to initial status.

In a second set of informal testing, volunteer testers provided the following information about their experiences.

Example 2A

Subject CH, who had had no food within the preceding two hours, had not consumed alcohol in the previous eight hours, who was on no other medications, and who gotten acceptable but not adequate sleep the night before ("so-so"), and who was self-described as a social consumer of *cannabis*, reported an overall feeling of 8.5 out of 10, a good mood, no tension, but a little pain in subject's foot. Subject consumed a sufficient amount of *cannabis* to self-describe as feeling a *cannabis* high, which subject rated as a level of 9 out of a possible 10. Subject described feeling "giddy, dehydrated, tingly, hyper focused, dissociated and creative." Subject reported no pain, that subject's body felt good, a good mood, a little fogginess, and no paranoia, anxiety or tension. Subject was "not sure" about subject's ability to solve a complex problem, and indicated subject's ability to handle an emergency was "so-so." Subject took a dose of one softgel of an embodiment of the invention described herein. Within three minutes, subject described an awareness of a reduction in subject's high. Subject further described that at ten minutes after taking the dose, the subject felt "about ¾ normal." Subject further described that at eighteen minutes after taking the dose, the subject reported a level of high at 1.5 out of a possible 10, that subject's body felt good, without pain, with no fogginess, and a serious but relaxed mood. The subject indicated that subject's ability to solve a complex problem was "better" and that subject's ability to handle an emergency was "good." At eighteen minutes and forty-five seconds after taking the dose, the subject reported the subject was "back to normal." At forty-three minutes after taking the dose, the subject reported "I'm thinking super sharp."

Example 2B

Subject DO, who not eaten within the preceding two hours, had not consumed alcohol in the previous eight hours, who was on no other medications, and who got adequate sleep the night before, and who did not report frequency of *cannabis* use, reported mild pain in the subject's joints, tension in subject's neck, and a mood of sadness. Subject consumed a sufficient amount of *cannabis* to self-describe as feeling a *cannabis* high, which subject rated as a level of 9 out of a possible 10. Subject described subject's feeling as "comfortable," "chill" and "relaxed." Subject described subject's body feeling as a 9, a slight fogginess, a very relaxed mood, and little paranoia, anxiety or tension. Subject described subject's ability to solve a complex problem as an 8 out of 10, but subject's ability to respond to an emergency as a 4 out of 10. Subject took a dose of one softgel of an embodiment of the invention described herein. Within ten minutes, subject described an awareness of a reduction in subject's high. At about thirty minutes after taking the dose, subject reported a level of high of 4.5 out of 10, rated the feeling of subject's body as a 9 out of 10, a fogginess of 3 out of 10, a mood as an 8 or 9 out of ten, an ability to solve a complex problem as 9 out of 10 and an ability to handle an emergency as a 6 or 7 out of 10.

Example 2C

Subject LS, who had had a meal within the preceding two hours, had not consumed alcohol in the previous eight hours, who was on an unspecified medication, and who got adequate sleep the night before, and who was self-described as a consumer of *cannabis* for pain relief and relaxation, reported a high level of pain in the subject's lower back, no tension in subject's body and an overall mood and feeling of "ok" and "10." Subject consumed a sufficient amount of *cannabis* to self-describe as feeling a *cannabis* high, which subject rated as a level of 10 out of a possible 10. Subject described feeling "relaxed," "happy" and "energized." Subject reported a significant lessening of pain, a "great" mood, no paranoia, anxiety or tension, but a level of fogginess of 7 out of 10. The subject reported subject's ability to solve a complex problem as a 7 out of 10 and subject's ability to handle an emergency as 10 out of 10. Subject took a dose of one softgel of an embodiment of the invention described herein. Within ten minutes, subject described an awareness of a reduction in subject's high. At about thirty minutes after taking the dose, subject reported a level of high of 3 out of 10, rated the feeling of subject's body 10 of 10, meaning no pain, a fogginess of 5 out of 10, a mood as 10 out of 10, an ability to solve a complex problem as 10 out of 10 and an ability to handle an emergency as a 10 out of 10. Subject also described subject's feeling as "relaxed" and "really chill."

Example 2D

Subject MB, who had not eaten within the preceding two hours, had not consumed alcohol in the previous eight hours, who was on an unspecified medication, and who got adequate sleep the night before, and who was self-described as a consumer of *cannabis* for the purpose of experiencing the high that it induces, reported having no pain, and an overall mood and feeling of 9 out of 10. Subject consumed a sufficient amount of *cannabis* to self-describe as feeling a *cannabis* high, which subject rated as a level of 9 out of a possible 10. Subject described feeling "great." Subject reported no pain, a mood of 10 out of 10, a slight feeling of paranoia, anxiety or tension, and a level of fogginess of 6 out of 10. The subject reported subject's ability to solve a complex problem as a 5 out of 10 and subject's ability to handle an emergency as 3 out of 10. Subject took a dose of one softgel of an embodiment of the invention described herein. Within thirteen minutes, subject described an awareness of a reduction in subject's high. At about thirty minutes after taking the dose, subject reported a level of high of 3 out of 10, stated that the feeling of subject's body was "slow/fine," a fogginess of 2 out of 10, a mood as 10 out of 10, an ability to solve a complex problem as 9 or 10 out of 10 and an ability to handle an emergency as a 1 to 3 out of 10. Subject also described his feeling as "smiling," "happy," and "loose." Subject noted that subject took a second capsule approximately an hour and nine minutes after the first. Subject noted that at an hour and thirty-five minutes after the first capsule, subject was "still not clear."

In a third set of informal testing, volunteer testers provided the following information about their experiences.

Example 3A

Subject Cris, who had had a light meal within the preceding two hours, had not consumed alcohol in the previous eight hours, who was on no other medications, and who got adequate sleep the night before, and who was self-described as a frequent consumer of *cannabis* for purposes of sleep, upset stomach and seeking a *cannabis* high, reported mild to moderate pain and tension in subject's body. Subject consumed a sufficient amount of *cannabis* to self-describe as feeling a *cannabis* high, which subject rated as a level of 6 out of a possible 10. Subject described subject's experience as doing little to alleviate subject's pain, creating a significant level of "fogginess", having very little ability to solve a complex problem, very little ability to respond to an emergency situation, slightly uncomfortable, somewhat tired, and some amount of paranoia. Subject took a dose of one softgel of an embodiment of the invention described herein. Within six minutes, subject described an awareness of a reduction in subject's high. Subject further described that subject's paranoia was "going away," that subject felt "comfortable," "fine," "happy" and "ok," and that subject still felt "loose." By twenty-four minutes after taking the embodiment of the present invention, subject reported that he no longer felt tired.

Example 3B

Subject SAL, who had no food within the preceding two hours, had not consumed alcohol in the previous eight hours, who was on no other medications, and who got adequate sleep the night before, and who was self-described as a daily consumer of *cannabis* for purposes of recreation and relaxation, reported mild pain and tension in subject's body. Subject consumed a sufficient amount of *cannabis* to self-describe as feeling a *cannabis* high, which subject reported as a level of 7 out of a possible 10. Subject described subject's level of pain or tension as mild, and moderate level of "fogginess." Subject also self-described subject's ability to solve a complex problem or respond to an emergency as very high. Subject also self-described subject's feeling as "relaxed," "calm," "confident," and "funny," but noted the sensation that "legs sometimes disappear." Subject took a dose of one softgel of an embodiment of the invention described herein. Within fifteen minutes, subject described an awareness of a reduction in subject's high. Subject further described slight sadness that the high was over.

Example 3C

Subject KL who had had a meal within the preceding two hours, had consumed one alcoholic beverage in the previous eight hours, who was on no other medications, and who got adequate sleep the night before, and who was self-described as consuming *cannabis* approximately twice a month, reported a good mood and moderate pain in subject's toe. Subject consumed a sufficient amount of *cannabis* to self-describe as feeling a *cannabis* high, which subject reported as a level of 8 out of a possible 10. Subject described subject's level of pain or tension as low, and moderate level of "fogginess." Subject also self-described subject's ability to solve a complex problem as moderate, and subject's ability to respond to an emergency as low. Subject also self-described subject's feeling as "feel like laughing," "releases the mind," and "fuzzy." Subject took a dose of one softgel of an embodiment of the invention described herein. Within seven minutes, subject described an awareness of a reduction in subject's high. Subject further described a decrease in the level of "fogginess" and a feeling of "lots of clarity" and an ability to follow complex conversations.

Example 3D

Subject WL who had had a meal within the preceding two hours, had consumed three sips of an alcoholic beverage in the previous eight hours, who was on statin medication for blood pressure and thyroid issues, and who got adequate sleep the night before, and who was self-described as consuming *cannabis* in the amount of "2-3 hits" daily, for purposes of relaxation, reported a moderate mood and moderate pain, but high levels of tension in the body. Subject consumed a sufficient amount of *cannabis* to self-describe as feeling a *cannabis* high, which subject reported as a level of 9 out of a possible 10. Subject described subject's level mood as excellent, pain and tension as essentially unchanged, and high level of "fogginess." Subject also self-described subject's ability to solve a complex problem as high, and subject's ability to respond to an emergency as very high. Subject took a dose of one softgel of an embodiment of the invention described herein. Within five minutes, subject described an awareness of a reduction in subject's high. Subject further described feeling of being "clear" and "energized."

Example 3E

Subject Hamed who had had a meal within the preceding two hours, had not consumed alcohol in the previous eight hours, who was on no other medications, and who got adequate sleep the night before, and who was self-described as consuming *cannabis* three to four times per week, reported feeling "stressed" and having tension in subject's upper and lower body, but no pain. Subject consumed a sufficient amount of *cannabis* to self-describe as feeling a *cannabis* high, which subject reported as a level of 9 out of a possible 10. Subject described subject's level of tension lessened, and high level of "fogginess." Subject also self-described subject's ability to solve a complex problem as low, and subject's ability to respond to an emergency as low. Subject also self-described subject's feeling as "relaxed" and "very" high. Subject took a dose of one softgel of an embodiment of the invention described herein. Within twenty-four minutes, subject described an awareness of a reduction in subject's high. Subject further described a decrease in the level of "fogginess" to low, no pain, little to no tension in subject's body and an increase in subject's ability to perform complex tasks or respond to an emergency to a moderate level.

Example 3F

Subject Leah who had not had a meal within the preceding two hours, had not consumed alcohol in the previous eight hours, who was on no other medications, who did not have adequate sleep the night before, and who did not report the frequency of her *cannabis* consumption, but did report consuming *cannabis* for purposes of relaxation, reported a good mood, some pain in her right hip, and neck and shoulder tension. Subject consumed a sufficient amount of *cannabis* to self-describe as feeling a *cannabis* high, which subject reported as a level of 11.5 out of a possible 10. Subject described subject's level of pain and tension as nonexistent, and reported feeling "tipsy," but also reported anxiety and rapid breathing. Subject also self-described her high as "Life feels like I need to recover from it." Subject took a dose of one softgel of an embodiment of the invention described herein. Within three minutes, subject described an awareness of a reduction in subject's high. Subject further described that she "was tipsy—now centering."

Example 3G

Subject ID who had not had a meal within the preceding two hours, had not consumed alcohol in the previous eight hours, who was on no other medications, and who got adequate sleep the night before, and who was self-described as consuming *cannabis* frequently, reported a moderately good mood. Subject consumed a sufficient amount of *cannabis* to self-describe as feeling a *cannabis* high, which subject reported as a level of 9 out of a possible 10. Subject described subject's level of pain or tension as low, and a low level of "fogginess." Subject also self-described subject's ability to solve a complex problem as moderate, and subject's ability to respond to an emergency as high. Subject also self-described subject's feeling as "like I am floating," and also reported a tingling sensation. Subject took a dose of one softgel of an embodiment of the invention described herein. Within four minutes, subject described an awareness of a reduction in subject's high. Subject further described an increase in subject's ability to solve a complex problem and that "I am feeling really nice right now."

Example 3H

Subject MW who had not had a meal within the preceding two hours, had consumed one alcoholic beverage in the previous eight hours, who was on no other medications, and who got adequate sleep the night before, and who was self-described as consuming *cannabis* that had a low level of THC and a high level of CBD (although frequency of use was not reported), reported a good mood and low level of pain or tension in subject's body. Subject consumed a sufficient amount of *cannabis* to self-describe as feeling a *cannabis* high, which subject reported as a level of 7 out of a possible 10. Subject described subject's level of pain or tension as low, and moderate level of "fogginess." Subject also self-described subject's ability to solve a complex problem as moderate, and subject's ability to respond to an emergency as moderate. Subject also self-described subject's feeling as "high" and that it was a "head high-detached." Subject took a dose of one softgel of an embodiment of the invention described herein. Subject described an awareness of a reduction in subject's high, but did not report the time at which that awareness occurred. Subject further described a slight increase in the level of "fogginess" and an increase in the ability to solve complex problems or respond to an emergency. The subject also reported that "body is very relaxed, and no head high."

Example 3I

Subject S who had had a meal within the preceding two hours, had consumed one alcoholic beverage in the previous eight hours, who was on no other medications, and who got adequate sleep the night before, and who was self-described as consuming *cannabis* approximately twice a month, reported a good mood and moderate pain in subject's toe. Subject consumed a sufficient amount of *cannabis* to self-describe as feeling a *cannabis* high, which subject reported as a level of 8 out of a possible 10. Subject described subject's level of pain or tension as low, and moderate level of "fogginess." Subject also self-described subject's ability to solve a complex problem as moderate, and subject's ability to respond to an emergency as low. Subject also self-described subject's feeling as "feel like laughing," "releases the mind," and "fuzzy." Subject took a dose of one softgel of an embodiment of the invention described herein. Within seven minutes, subject described an awareness of a reduction in subject's high. Subject further described a decrease in the level of "fogginess" and a feeling of "lots of clarity" and an ability to follow complex conversations.

One embodiment of the present invention for administration of a therapeutically effective amount of Olivetol comprises one softgel, containing the following formulation:

30 mg Olivetol
750 mg Olive oil
10 mg Vitamin E

A dose may be considered either 1 or 2 capsules, as needed. In one embodiment, the oil and Olivetol formulation is encapsulated in gelatin-based "softgel" capsules. In another embodiment, the dose is formulated in a vegetable-based capsule so that it may be taken by vegetarians. Other embodiments include a combination of a therapeutically effective dose of Olivetol, combined with an edible oil, in a capsule, such as a hard shell capsule, a soft gel capsule, a caplet or a tablet. Embodiments of the invention may include an oil soluble anti-oxidant. Such an antioxidant is useful for preserving the shelf-life of the oil, particularly oils listed above that may spoil or go rancid when stored at room temperature.

For alternative embodiments, it would be suitable to use any oil that is liquid at room temperature, with the preferred oils having the longest shelf life. Vitamin E is a powerful, fat-soluble antioxidant included to reduce oxidation over time, thereby increasing shelf life. For alternative commercial embodiments, other suitable fat-soluble antioxidants may be used. A non-limiting list of such alternative fat soluble antioxidants includes Vitamin A, Carotenes, Lutein, Lycopene, Cryptoxanthin, lipoic acid, and known substitutes for each.

Alternative embodiments of the present invention for administration of a therapeutically effective amount of Olivetol comprise one softgel, containing one or more of the following formulations. For each such formulation, additional known or anticipated beneficial health effects are stated:

(a) Olivetol—50 mg
  Lecithin—50 mg
  Olive oil—700 mg
  Vitamin E—10 mg
  Health Effects or Benefits: Extra strength, rapid relief, good for cholesterol control.
(b) Olivetol—40 mg
  Coconut oil—200 mg
  Olive oil—550 mg
  Vitamin E—10 mg
  Health Effects or Benefits: Antioxidant, good for cholesterol control.
(c) Olivetol—30 mg
  Coconut oil—200 mg
  Avocado oil—550 mg
  Vitamin E—10 mg
  Health Effects or Benefits: Anti-inflammatory, heart healthy.
(d) Olivetol—40 mg
  Avocado oil—200 mg
  Olive oil—550 mg
  Vitamin E—10 mg
  Health Effects or Benefits: Anti-oxidant, anti-inflammatory, good for cholesterol control.
(e) Olivetol—30 mg
  Sesame oil—150 mg
  *Macadamia* oil—50 mg
  Avocado oil—550 mg
  Vitamin E—10 mg
  Health Effects or Benefits: Anti-oxidant, anti-inflammatory, energy boosting.
(f) Olivetol—50 mg
  Coconut oil—250 mg
  *Macadamia* oil—250 mg
  Avocado oil—250 mg
  Vitamin E—10 mg
  Health Effects or Benefits: Energy boosting, immune system boosting, heart healthy.
(g) Olivetol—40 mg
  Almond oil—200 mg
  Coconut oil—400 mg
  Sesame oil—150 mg
  Vitamin E—10 mg
  Health Effects or Benefits: Anti-oxidant, anti-inflammatory, anti-bacterial.
(h) Olivetol—30 mg
  Avocado oil—200 mg
  Hemp seed oil—400 mg
  Pumpkin oil—150 mg
  Vitamin E—10 mg
  Health Effects or Benefits: Anti-oxidant, anti-inflammatory, anti-diabetic effects, heart healthy.
(i) Olivetol—40 mg
  Avocado oil—250 mg
  Hemp seed oil—250 mg
  Coconut oil—250 mg
  Vitamin E—10 mg
  Health Effects or Benefits: Heart healthy, supports the immune system, anti-bacterial.
(j) Olivetol—30 mg
  Avocado oil—200 mg
  Hemp seed oil—200 mg
  Olive oil—350 mg
  Vitamin E—10 mg
  Health Effects or Benefits: Heart healthy, supports immune system, good for cholesterol control.
(k) Olivetol—40 mg
  Almond oil—100 mg
  Hemp seed oil—200 mg
  Coconut oil—200 mg
  Olive oil—250 mg
  Vitamin E—10 mg
  Health Effects or Benefits: Anti-oxidant, supports immune system, heart healthy, good for cholesterol control.
(l) Olivetol—40 mg
  Sesame oil—150 mg
  Almond oil—200 mg
  *Macadamia* oil—200 mg
  Avocado oil—200 mg
  Vitamin E—10 mg
  Health Effects or Benefits: Anti-inflammatory, heart healthy.
(m) Olivetol—50 mg
  Almond oil—300 mg
  Avocado oil—300 mg
  Poppy seed oil—50 mg
  *Macadamia* oil—100 mg
  Vitamin E—10 mg
  Health Effects or Benefits: Heart healthy, calming, anti-inflammatory.
(n) Olivetol—40 mg
  Olive oil—200 mg
  Acai oil—50 mg
  Blackcurrant oil—50 mg
  Almond oil—450 mg
  Vitamin E—10 mg
  Health Effects or Benefits: Heart healthy, anti-oxidant.
(o) Olivetol—30 mg
  Almond oil—150 mg
  *Macadamia* oil—150 mg
  Walnut oil—150 mg
  Pistachio oil—150 mg
  Sesame oil—150 mg
  Health Effects or Benefits: Heart healthy, anti-bacterial.
(p) Olivetol—40 mg
  Sesame oil—50 mg
  Olive oil—200 mg
  Avocado oil—100 mg
  *Macadamia* oil—200 mg
  Artichoke oil—200 mg
  Health Effects or Benefits: Heart healthy.

In other embodiments of the invention, other nutraceuticals, vitamins, minerals, herbs herbal extracts, or essential oils may be added to the combination of Olivetol and edible oil, in order to promote or provide certain nutrients, minerals, supplement effects or health benefits, in addition to the effects of the Olivetol and edible oil combination described herein.

In embodiments of the invention, preferably, the Olivetol is between 97-98% pure. However, lower purity may be acceptable, particularly if the amount used per dose is increased.

An alternative embodiment for a method of delivery of Olivetol is through the use of liposomal delivery. A liposome is a spherical vesicle having at least one lipid bilayer. The liposome can be used as a vehicle for administration of nutrients and pharmaceutical drugs. Liposomes can be prepared by disrupting biological membranes (such as by sonication). Liposomes are most often composed of phospholipids, especially phosphatidylcholine, but may also include other lipids, such as egg phosphatidylethanolamine, so long as they are compatible with the lipid bilayer structure.

In some embodiments, Olivetol may be included in liposomes made from phospholipids. These encapsulating phospholipids containing Olivetol, when delivered orally/sublingually or intravenously, bond with cell membranes to facilitate intracellular delivery. Liposomes may be formed from lecithin, or high-phosphatidylcholine phospholipid mixes, as will be appreciated by one of skill in the art. Further, phospholipid particle size may vary according to different embodiments, ranging from 50 nm to 600 nm, but more preferably ranging from 50 nm to 100 nm. Embodiments of this delivery method of the present invention may be suspended in a suitable carrier (such as an aqueous solution or a tincture), and either sprayed into the subject's mouth, or injected intravenously.

Additional embodiments of the present invention include the addition of flavorings or flavor blockers, addition of the Olivetol to an oil-based candy or edible, or other suitable delivery methods for oil-based nutraceuticals, including as an edible oil/Olivetol combination to be administered orally by drinking.

Preferably, the Olivetol used in the present invention should not be heated prior to use and should be stored at room temperature or cooler.

While a dose of between 4 mg-200 mg is therapeutically effective for most persons, in certain circumstances it may be desirable to deliver higher dosages. In particular, when a person has consumed an extreme amount of THC, or is suffering from anxiety, panic, or is experiencing a psychotic episode, it may be advisable to administer an oral dose of purified Olivetol of as much as 10-15 milligrams per kilogram of body weight. Thus, for an average person, based on an estimated average weight in North America of approximately 80 kg, a higher dose may approach 800-1000 mg. Ranges of high dosages that may be beneficial, include, without limitation, 200 mg-1000 mg, 200 mg-800 mg, 200 mg-600 mg, 200 mg-400 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, and all dosages within these ranges, depending upon the person's response, or lack thereof, to lower dosages.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments disclosed.

What is claimed is:

1. A method of reducing the psychoactive effects of tetrahydrocannabinol (THC) in humans comprising the step of orally administering a therapeutically-effective dose of Olivetol, before or after consumption of THC, wherein said dose is between 200 mg and 1000 mg.

2. The method of claim 1, wherein said dose is between 200 mg and 800 mg.

3. The method of claim 1, wherein said dose is between 200 mg and 700 mg.

4. The method of claim 1, wherein said dose is between 200 mg and 600 mg.

5. The method of claim 1, wherein said dose is between 200 mg and 500 mg.

6. The method of claim 1, wherein said dose is between 200 mg and 400 mg.

7. The method of claim 1, wherein said dose is 200 mg.

8. The method of claim 1, wherein said dose is 250 mg.

9. The method of claim 1, wherein said dose is 300 mg.

10. The method of claim 1, wherein said dose is 350 mg.

11. The method of claim 1, wherein said dose is 400 mg.

12. The method of claim 1, wherein said dose is 500 mg.

13. The method of claim 1, wherein said dose is 600 mg.

14. The method of claim 1, wherein the dose is 700 mg.

15. The method of claim 1, wherein the dose is 800 mg.

16. The method of claim 1 wherein the step of orally administering comprises administering a softgel containing the therapeutically-effective dose of Olivetol.

17. The method of claim 16 wherein the softgel further comprises an edible oil.

18. The method of claim 17 wherein the softgel further comprises an anti-oxidant.

19. The method of claim 18 wherein the anti-oxidant comprises Vitamin E.

20. The method of claim 1 wherein the step of orally administering comprises administering a plurality of softgels, which in combination, contain the therapeutically-effective dose of Olivetol.

* * * * *